(12) United States Patent
Goldmann

(10) Patent No.: US 6,447,551 B1
(45) Date of Patent: Sep. 10, 2002

(54) FLAT IMPLANT, PROCESS FOR ITS PRODUCTION AND USE IN SURGERY

(75) Inventor: Helmut Goldmann, Tuttlingen (DE)

(73) Assignee: Aesculap AG & Co. KG, Tuttlingen/Donav (DE)

( * ) Notice: Subject to any disclaimer, the term of this patent is extended or adjusted under 35 U.S.C. 154(b) by 0 days.

(21) Appl. No.: 09/531,842

(22) Filed: Mar. 20, 2000

(30) Foreign Application Priority Data

Mar. 20, 1999 (DE) .......................................... 199 12 648

(51) Int. Cl.[7] ................................................. A61F 2/36
(52) U.S. Cl. ..................................... 623/23.76; 606/213
(58) Field of Search .......................... 623/23.76, 23.64, 623/23.72, 23.75, 23.74, 11.11; 606/213; 600/37; 602/49

(56) References Cited

U.S. PATENT DOCUMENTS

| 3,878,565 A | 4/1975 | Saeuvage | |
|---|---|---|---|
| 4,047,252 A | 9/1977 | Liebig et al. | |
| 4,193,397 A | 3/1980 | Tucker et al. | |
| 4,517,687 A | 5/1985 | Liebig et al. | |
| 5,002,582 A | 3/1991 | Guire et al. | |
| 5,358,475 A | * 10/1994 | Mares et al. | 623/66 |
| 6,166,286 A | * 12/2000 | Trabucco | 623/11 |
| 6,264,702 B1 | 7/2001 | Ory et al. | 623/23.75 |

FOREIGN PATENT DOCUMENTS

| CA | 2114282 | 7/1994 |
|---|---|---|
| DE | 2461370 | 7/1975 |
| DE | 2827450 | 1/1979 |
| DE | 3107189 | 12/1981 |
| DE | 3128815 | 6/1982 |
| DE | 3324256 | 1/1985 |
| DE | 3801426 | 8/1989 |
| DE | 19809054 | 1/1999 |
| FR | 2145975 | 2/1973 |
| FR | 2524304 | 7/1983 |
| WO | 8908467 | 9/1989 |
| WO | 9014810 | 12/1990 |
| WO | 9210218 | 6/1992 |
| WO | 9849967 | 11/1998 |
| WO | 9906079 | 2/1999 |
| WO | 9951163 | 10/1999 |

* cited by examiner

Primary Examiner—David J Isabella
Assistant Examiner—Urmi Chattopadhyay
(74) Attorney, Agent, or Firm—Baker Botts L.L.P.

(57) ABSTRACT

A flat implant for use in surgery is described. The implant includes a flexible fabric comprising two sides and having on one side a substantially closed surface and on the other side a three-dimensional microstructure permitting a growing in of cells. The implant can be more particularly used for the treatment of wall defects in body cavities, such as abdominal wall defects.

20 Claims, 2 Drawing Sheets

FLAT IMPLANT, PROCESS FOR ITS PRODUCTION AND USE IN SURGERY

DESCRIPTION

Figure 1:
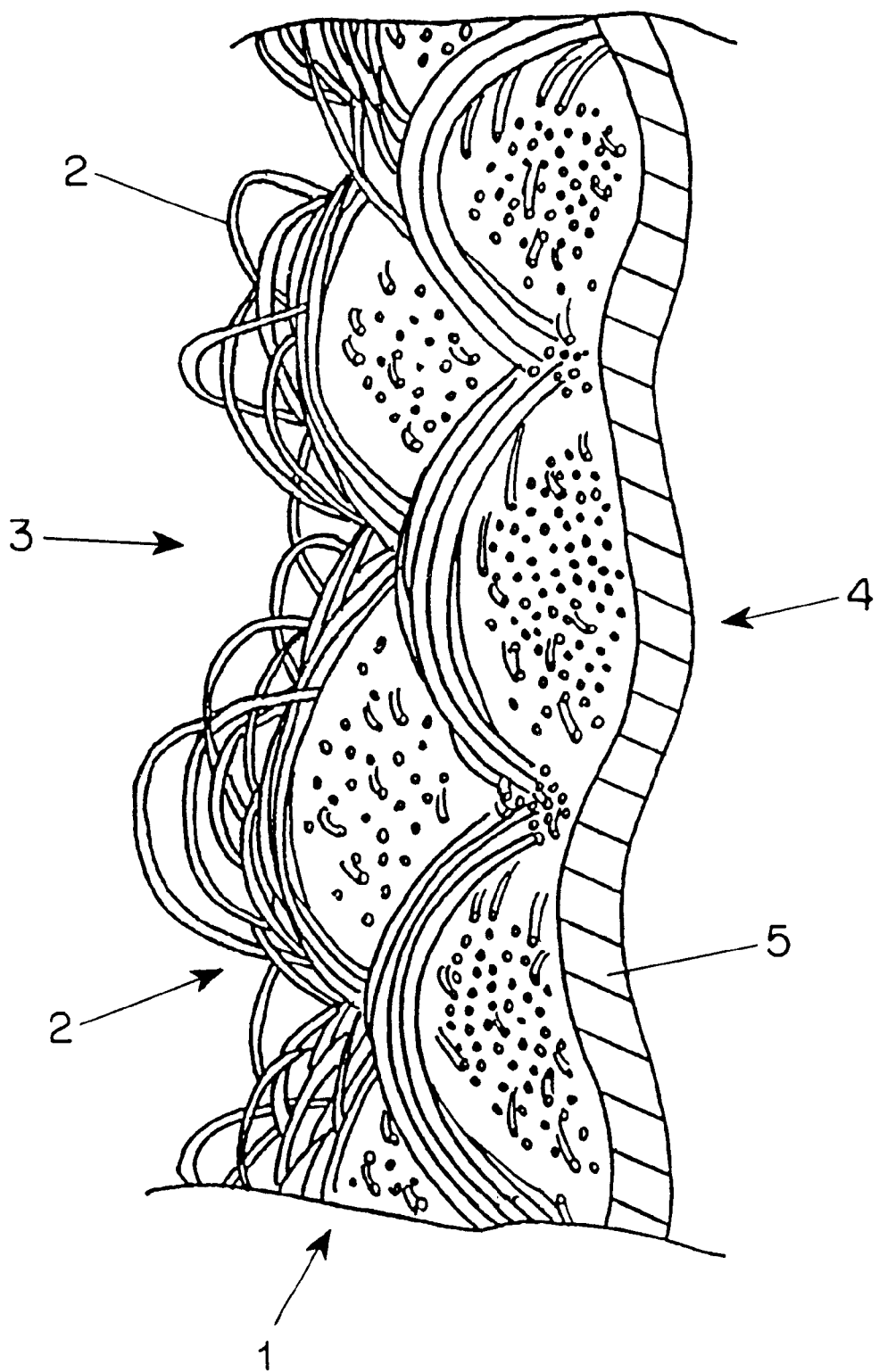

The present invention relates to a flat implant, a process for its production and its use in surgery.

Hernia is a frequently encountered illness. It generally consists of a passage of organs or organ parts out of the natural body cavity through a preformed or acquired gap. Among external hernias, where the hernial sac is always surrounded by the peritoneum, the most frequently encountered forms are groin, umbilical and incisional hernias. The reason for hernias occurring are in particular muscle or connective tissue weaknesses in conjunction with overstressing, age-caused atonia, congenital weakness of the abdominal wall or inadequate cicatrization following a body section (incisional hernia).

In most cases effective treatment by surgery is possible, where the hernia content is transferred back from the hernial sac into the abdomen and the hernial opening is closed. This closure of the hernial opening normally takes place by a suture.

However, this surgical procedure suffers from the disadvantage that in up to 20% of cases a further hernia occurs, i.e. the so-called hernial relapse.

Due to this unsatisfactory relapse rate following conventional hernia operations, in modern hernia surgery increasing use is being made of artificial strengthening materials for the reconstruction of the abdominal wall. Polypropylene and also polyester nets play an important part.

Although the use of such nets has clearly led to a marked decrease in the relapse rate, such implants are not unproblematical due to possible infections or fistula formations and in particular due to the soft tissue adhesion risk.

The hitherto known implants consist of open textile structures, which aid an adhesion of cells and also a growing through of cells. This is advantageous, because it forms a firm connection between the implant and the abdominal wall and thus ensures the desired support function. However, it can lead to difficultly removable cicatrizations in the abdominal cavity with hardening effects, detrimental action on the intestine and internal organs and the associated complaints on the part of the patient.

Flat, textile implants are also known, which are sealed with an impregnating agent. However, problems then arise in fixing to the abdominal wall, particularly when spending a long time in the body.

The problem is to make available an implant for use in surgery, which overcomes the difficulties of prior art implants, which is easy and inexpensive to manufacture and which is usable by employing conventional surgical methods.

Accordingly, it is an object of this invention to provide a flat implant comprising a flexible fabric comprising two sides and having on one side a substantially closed surface and on the other side a three-dimensional microstructure permitting a growing in of cells, wherein the substantially closed surface comprises micropores, wherein the micropores permit an exchange of materials and are sufficiently small to prevent the growing in of cells, the closed surface being formed by a surface layer connected to the flexible fabric as a coating formed by spray coating of a web of a polymer, and the three-dimensional microstructure having back-engagement points for the growing in of cells formed by at least one of a woven fabric and a knitted fabric, the implant having an air permeability of 5 to 100 ml of air/$cm^2$.min at a pressure difference of 1.2 kpascal. The implant according to the invention permits a good anchoring of body cells on the structured side facing the abdominal wall and prevents an undesired cicatrization with organs and body parts on the substantially closed side facing the abdominal cavity. It is another object of this invention to provide a method for the production of the implant by forming a unilaterally closed surface on one side of a porous, particularly textile fabric for preventing the growing in of cells.

For use in surgery the invention provides a flat implant to be used with a flexible fabric, which has on one side a substantially closed surface and on the other side a three-dimensional microstructure permitting the growing in of cells. In particular, the substantially closed surface can be microporous, the micropores being so small that they allow an exchange of material, but substantially prevent the growing in of cells.

Preferably the substantially closed surface is smooth. The substantially closed surface can also be formed by a surface layer connected to the flexible fabric, particularly a coating of said fabric.

According to the invention, the three-dimensional microstructure can have back-engageable points for the growing in of cells. Advantageously the flexible fabric is formed by a porous, flexible structural material, particularly a flexible support and the three-dimensional microstructure is formed by the exposed surface structure of the structural material. Examples of porous, flexible structural materials are open-cell structural foam or a lattice structure.

Advantageously the implant is formed by at least one synthetic polymer material. Preferably the fabric of the implant according to the invention is formed from polypropylene, polyester, polytetrafluoroethylene and/or polyester and polytetrafluoroethylene. Particular preference is given according to the invention to a flat polyester and polytetrafluoroethylene implant. It is also possible to use resorbable materials such as polylactides, polyglycolides and copolymers thereof, if a resorbability or partial resorbability is desired.

In an embodiment of the invention the flexible structural material can be a textile material, particularly a porous textile support. Preferably the flexible textile support at least on the side with the three-dimensional microstructure has an open textile structure known in connection with vascular implants and which is in particular formed by textured yarns, float stitches and/or velours loops, such as are e.g. known from U.S. Pat. No. 4,047,252, U.S. Pat. No. 3,878,565, DE 2,461,370 and U.S. Pat. No. 4,517,687.

It is possible to process shrinkable fibers and yarns produced therefrom such as other fibers and yarns using conventional procedures so as to give textile fabrics. Subsequently as a result of shrinkage treatment the shrinkable fibers are shrunk, which in the case of the textile fabric produced therefrom leads to a compression of the structure. As a result of the planned use of shrinkable fibers and non-shrinkable fibers in the combination, it is possible in planned manner to effect modifications to the textile structure.

It is possible to process shrinkable fibres and yarns produced therefrom such as other fibres and yarns using conventional procedures so as to give textile fabrics. Subsequently as a result of a shrinkage treatment the shrinkable fibres are shrunk, which in the case of the textile fabric produced therefrom leads to a compression of the structure.

As a result of the planned use of shrinkable fibres and non-shrinkable fibres in combination, it is possible in planned manner to effect modifications to the textile structure.

According to the invention the fabric can be produced according to a textile method, particularly knitting, weaving or braiding. Such procedures are known to the expert, so that there is no need for a detailed explanation here. This permits a simple, inexpensive manufacture according to known, proven procedures and using conventional machines and tools.

Advantageously the flexible textile fabric, particularly the textile support, can be a woven fabric or in particular a knitted fabric, which at least on the three-dimensionally structured side has exposed fibres or threads serving to anchor the cells.

It is possible to use textile fibrous materials such as synthetic monofilaments, multifilament threads or multifilament yarns. Preferably, according to the invention, the fabric can at least partly be formed from multifilament yarns, which can be smooth or structured. In an embodiment of the invention the yarns can be formed from a single fibrous material type. In another embodiment the yarns can be formed from several fibrous materials. The yarns can at least partly be formed from highly shrinkable fibrous material. They can also be blends of non-resorbable and resorbable fibrous materials.

The implant according to the invention can in particular be characterized in that one face is formed with a structured surface. According to a preferred embodiment the structured surface can be in velours form. In a particularly preferred embodiment of the invention the fabric can be constructed as velours, particularly single velours. According to a further development of the particularly preferred embodiment the fabric can be constructed as double velours. In particular, the double velours can be constructed with different pile heights on both sides of the fabric.

In a preferred embodiment of the invention the flexible fabric, particularly the textured support can be a velours, particularly a double velours, a double velours having on the structured side preferably a greater pile height than on the substantially closed side of the implant.

According to the invention, the flat implant can be characterized in that the side opposite to the structured surface is constructed as a smooth surface. In this case smooth means that the surface has no structuring, i.e. as a result of the textile construction, which permits an anchoring of cell unions. Smooth also means that no fibres of the textile material used project from the surface.

According to the invention, the implant is preferably in the form of a composite structure of two or more different layers. In an embodiment the substantially closed surface can be formed by coating with synthetic material. According to the invention, the coating is preferably constructed as a sprayed coating.

In an embodiment the coating can be a sprayed coating, particularly a sprayed web of a polymer, particularly a polymer soluble or dispersible in a nonaqueous, liquid and preferably volatile medium. In this way it is possible to form a microporous sprayed web, in which initially dissolved sprayed particles are connect ed with one another and to the surface of the fabric. Advantageously the substantially closed surface layer is of polyurethane, particularly uncrosslinked polyurethane. Polylactides and copolymers thereof can also be sprayed from chloroform, instead of polyurethane or mixed therewith, if a resorbability or partial resorbability is desired.

In another embodiment the substantially closed surface can be formed by the application of a polymer film. Such a polymer film can advantageously be constructed as a microporous film. A suitable material for a polymer film for modifying the implant according to the invention can be a biocompatible material suitable for the intended use as a surgical implant and preferably polypropylene, polyester, polytetrafluoroethylene and/or polyurethane. The application of a synthetic material film for modifying the surface of the textile fabric according to the invention can take place by procedures such as e.g. calender coating or sticking on.

In another embodiment of the invention the implant can be formed by a three-dimensional web, fibrous materials on the side with the substantially closed surface being closely juxtaposed and on the side with the microstructure form an open union.

The substantially closed sur face can be completely tight. If, as preferred, it is microporous, then compared with the porosity of the fabric, it is characterized by a porosity lower by at least a power of 10. In particular, the sprayed coating preferred according to the invention has a deep porosity. Advantageously the substantially closed surface and in particular the complete implant has an air permeabilty of 5 to 100 ml of air/cm$^2$.min, particularly 25 to 75 ml of air/cm$^2$.min, in the case of a pressure difference of 1.2 kpascal. With such a microporosity an exchange of material in the molecular range is possible. This aids metabolic processes in the vicinity of the implant, aids the supply of essential nutrients and build-up substances, as well as the removal of metabolic waste and harmful substances. This advantageously permits a good compatibility and successful healing. The microporosity of the substantially closed surface is not, however, suitable for the passage or firm and continuous anchoring of large particles such as cells.

The inventive, substantially closed surface leads to a reduction of the structuring of the implant surface on one side. Protuberances and depressions, which e.g. result from the textile fabric manufacturing process, are compensated by the substantially closed, particularly smooth surface. In addition, individual fibres projecting from the textile fabric are enclosed. The closing of the implant surface according to the invention can consequently be considered as a type of surface sealing.

In this way, the substantially closed surface with its limited porosity and small surface structure is unfavourable for an adhesion of cells. The cells find no suitable anchoring points which are necessary for their growth. This essentially prevents a colonization by cells of the substantially closed implant surface.

The implant according to the invention preferably has fraying-proof edges or borders, which are processed or woven, particularly welded so as to be fraying-proof.

Advantageously the implant can have a total thickness of approximately 0.1 to 1.2 mm, the thickness of the substantially closed surface being 3 to 15% thereof. The textile support can have a woven or knitted basic weave with a thickness of 0.05 to 0.4 mm and an at least unilateral open structure with a thickness of 0.05 to 0.8 mm.

According to the invention, all the components of the implant are biocompatible and long term-stable. In particular, it can be partly resorbable over the entire surface and in particular the substantially closed surface can comprise completely resorbable material. Thus, following implantation in a physiological medium of the body, there is no surface degradation. The substantially closed surface of the implant consequently maintains its cell-rejecting characteristics, which prevent an adhesion and growing in of cells, such as is provided in accordance with the invention.

Advantageously the implant according to the invention is made from flexible material. Preferably the substantially closed surface can be formed from a solvent-soluble, uncrosslinked polymer. According to a further development the substantially closed surface can be formed with a rubbery polymer. Preferably, according to the invention, the substantially closed surface can be applied in the form of a solution in a low-boiling solvent to one side of an in particular textile fabric. According to a particularly preferred embodiment of the invention the substantially closed surface of the flat implant can be formed from uncrosslinked polyurethane.

According to a further development the implant can contain an antimicrobiotic substances, such as e.g. an antibiotic. The administration of antibiotics serves in particular to prevent infections. For prophylaxis and therapy with antibiotics in the surgical field use is e.g. made of cephalosporins such as cephazolin or cephamandol, netilmicin, penicillins such as oxacillin or mezlocillin, tetracycline, metronidazol or aminoglycosides such as gentamicin or neomycin, as well as e.g. rifampicin. In accordance with the particular requirements, experts can select one or more suitable active substances for use. The implant can also contain growth factors.

The present invention also relates to a process for the production of an implant for use in surgery, which comprises the formation of a unilateral, substantially closed surface on one side of a porous, particularly textile fabric for preventing the growing in of cells.

In another embodiment, the invention relates to a process for the production of an implant for use in surgery by forming a substantially closed surface layer and unilaterally, in particular a building-up formation of a three-dimensional microstructure connected thereto.

According to a preferred inventive process, the substantially closed surface can be formed by coating, particularly spray coating. In a preferred embodiment of the inventive process the polyurethane can be sprayed from a solution in low-boiling, organic solvent. Examples of suitable solvents are methylene chloride and chloroform. By evaporating the solvent the coating film forms. During solvent evaporation fine pores can form in the surface coating, which is advantageous for the implant according to the invention. The thus formed microporosity allows the exchange of materials in the physiological medium. However, the pores are so small that cells are held back.

According to the invention there is a closing of the surface for preventing the growing in of cells on only one side of the flat implant and on only the surface of the fabric. Advantageously the three-dimensionally structured surface of the textile fabric is open and suitable for a growing in of cells. The porous or structured surface is suitable for an adhesion and growing of cells and permits a back-engaging growing in of the cells.

For use in surgery the inventively modified implant can be appropriately sterilized. An appropriate sterilization process can be selected from conventional physical or chemical methods for the inactivation of microorganisms or can be a combination of such methods. One possible sterilization process comprises treatment with ionizing rays, such as e.g. irradiation with $\beta$ rays or $\delta$ rays, in the range 0.1 to 10 Mrad, particularly 0.8 to 2.5 Mrad.

The invention also relates to the use of an implant in surgery, particularly for the treatment of wall defects in body cavities, particularly abdominal wall defects.

To this end the inventively modified implant material can be cut to a desired size and shape. Advantageously the surgical implant according to the invention is available appropriately packed, ready for use and cut to an appropriate size.

The introduction of the inventive flat implant into the abdominal cavity takes place in such a way that the implant side, whose surface is modified for preventing the growing in of cells, is inserted towards the inside of the abdomen, i.e. facing the intestines. The opposite side of the flat implant, where a growing in of cells is possible, is inserted facing the abdominal wall side.

Thus, during the healing process, from the abdominal wall body cells can adhere to the implant surface, penetrate the surface structure and over a period of time lead to the cicatrization of the implant with the abdominal wall. This leads to a reliable union between the abdominal wall and the implant, which contributes to the stabilization of the abdominal wall and therefore ensures a successful treatment.

The substantially closed surface for preventing the growing in of cells on the implant abdomen inside is not penetratable by cells growing in from the abdominal wall side.

Further features of the invention can be gathered from the following description of a preferred example in conjunction with the subclaims and drawing. The individual features, both singly and in the form of combinations, can be implemented in an embodiment of the invention. However, the example only serves to illustrate the invention and does not restrict the latter.

FIG. 1 is a diagrammatic section through an implant according to one embodiment of the invention.

Figure 2:
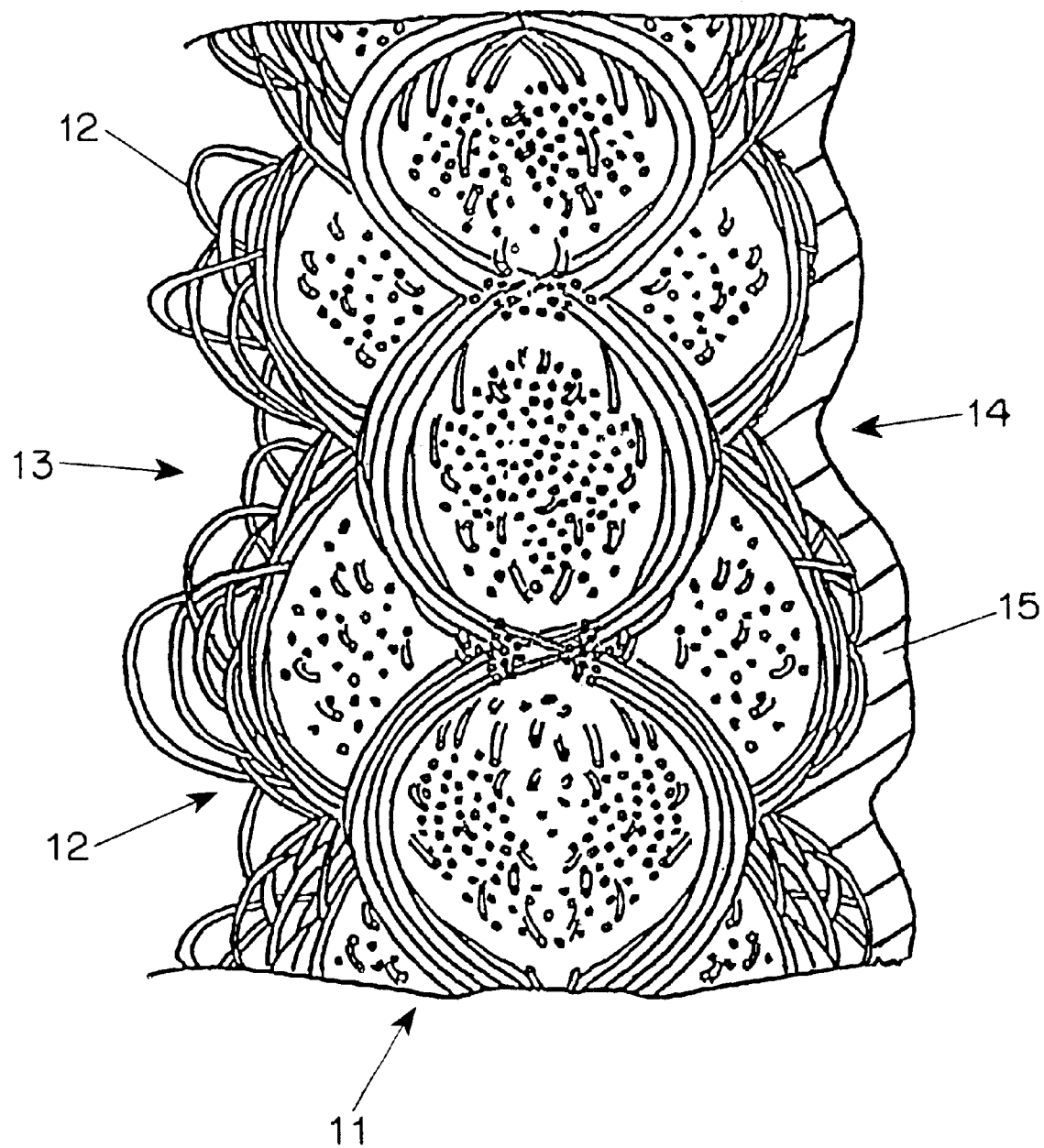

FIG. 2 is a diagrammatic section through an implant according to another embodiment of the invention in which the fabric is constructed in double velour form. In particular, FIG. 2 shows a double velour with velour loops 12 of texturized yarn on both sides. Side 13 of textile fabric 11 has an open three-dimensionally structured surface as also present in FIG. 1. Side 14 is also a velour side, which is coated with a spray coating 15 of uncrosslinked polyurethane.

EXAMPLE 1

A textile fabric 1 is constructed as warp knitwear from multifilament polyethylene terephthalate yarn in the form of a single velours, there being velours loops of textured yarn. The knitted fabric in double velours form can be constructed in similar manner to the knitted fabrics of U.S. Pat. Nos. 4,047,252 and 4,193,397. However, it is flat, unlike the tubular warp knitwear described therein. It can also be constructed as a single velours. The knitted fabric is porous and flexible. On the velours side 3 it has an open, three-dimensional structured surface, which as a result of the velours loops and texturing of the fibers, has numerous, substantially uniformly surface-distributed back-engagement possibilities for the growing in of body cells. The openings between the yam loops or the individual fibers are large compared with the size of the body cells. This permits the growing in of a cohesive cell union.

As a result of the texture of the knitted fabric, the opposite side 4 of the knitted fabric 1 is more dense and rather planar. Additionally the knitted fabric 1 has on this side a spray coating of uncrosslinked polyurethane, which is joined to the surface-exposed fibers of the knitted fabric 1 and closes the textile structure on this surface. The thickness of the spray coating is approximately 1/10 to 1/20 of the total thickness of the textile fabric and sealing layer, i.e. the total thickness of the flat implant of approximately 0.8 mm.

As a result of spray coating, i.e. the spraying on of a solution of polyurethane in chloroform, the coating 5 has a structure which can be compared roughly to that of a tight web, is microporous and is also flexible as a result of the elastomeric characteristics of polyurethane. Suitable polyurethanes are e.g. known saturated polyesters and polyurethanes. As a result of the sealing layer 5 the textile fabric 1 of velours knitwear is substantially closed in the manner of a deep filter on the side directed away from the velours loops 2. The micropores, whose size is roughly of the same order of magnitude as the size of the body cells or smaller, permit an exchange of body fluids for maintaining the metabolism, but do not permit the growing in of cells, or at least not in a form such that it is necessary to fear an adhesion of body parts in the vicinity of the abdominal cavity.

The sealing layer 5 only penetrates insignificantly into the textile surface of the textile support 1, so that the three-dimensional volume of the fabric is available for the growing in of cells from the abdominal wall, whereas the substantially closed sealing layer 5 prevents such a growing in of cells on the abdominal cavity side.

Due to the knitting construction the edges of the fabric are already fraying-proof. The sealing layer prevents a rolling in of the knitted fabric and additionally prevents any fraying tendency. If desired, the edges can be rendered completely fraying-proof by welding the thermoplastic fibres. For use in surgery pieces with the approximate dimensions 8×2 cm to 30×30 cm are produced. As a function of needs, these pieces can be cut to size prior to implantation.

Animal tests carried out with the implant according to the invention have given good results. On the uncoated, open side of the implants, there was a very good incorporation into the tissue with powerful vascularization in the implant meshes and no repulsion phenomena. As a result of the sealing of the abdominal cavity-side surface, no cicatrization occurred on this side. Even after the implant had been in the abdominal cavity for a long time, a free mobility of the abdominal viscera relative to the implant was ensured.

What is claimed is:

1. A flat implant for use in surgery, the implant comprising a flexible fabric comprising two sides and having on one side a substantially closed surface and on the other side a three-dimensional microstructure permitting a growing in of cells, wherein the substantially closed surface comprises micropores, wherein the micropores permit an exchange of materials and are sufficiently small to prevent the growing in of cells, the closed surface being formed by a surface layer connected to the flexible fabric as a coating formed by spray coating of a web of a polymer, and the three-dimensional microstructure having back-engagement points for the growing in of cells formed by at least one of a woven fabric and a knitted fabric, the implant having an air permeability of 5 to 100 ml of air/cm$^2$.min at a pressure difference of 1.2 kpascal.

2. The implant according to claim 1, wherein the substantially closed surface is substantially smooth.

3. The implant according to claim 1, wherein the flexible fabric is formed by a porous, flexible structural material.

4. The implant according to claim 3, wherein the flexible structural material is a textile fabric.

5. The implant according to claim 4, wherein the textile fabric is a porous textile support.

6. The implant according to claim 3, wherein the flexible structural material has on at least the side with the three-dimensional microstructure an open textile structure.

7. The implant according to claim 3, wherein the flexible fabric is a flexible support and the three-dimensional microstructure is formed by the exposed surface of the structural material.

8. The implant according to claim 3, wherein the flexible structural material is a velour.

9. The implant according to claim 8, wherein the velour is a double velour, the double velour having on the side with the three-dimensional microstructure a larger pile height than on the substantially closed side of the implant.

10. The implant according to claim 1, wherein the coating is a sprayed web of a polymer, said polymer being one of soluble and dispersible in a medium, wherein the medium is at least one of non-aqueous, liquid, and volatile.

11. The implant according to claim 1, wherein the substantially closed surface coating is made of polyurethane.

12. The implant according to claim 11, wherein the polyurethane is uncrosslinked polyurethane.

13. The implant according to claim 1, wherein the implant has an air permeability of 25 to 75 ml of air /cm$^2$.min for a pressure difference of 1.2 kPascal.

14. The implant according to claim 1, wherein the implant has fraying-proof edges formed by one of processing, bonding, and welding in fraying-proof manner.

15. The implant according to claim 1, wherein the implant has a total thickness of approximately 0.1 to 0.2 mm, the thickness of the substantially closed surface being 3 to 15% thereof.

16. The implant according to claim 1, wherein the flexible fabric has at least one of a woven and knitted basic weave with a thickness of 0.05 to 0.4 mm and an at least unilaterally open structure with a thickness of 0.05 to 0.8 mm.

17. The implant according to claim 1, wherein the implant is partly resorbable.

18. The implant according to claim 17, wherein the substantially closed surface is of completely resorbable material.

19. The implant according to claim 1, wherein the flexible fabric comprises at least one of textured yarns, float stitches, and velour loops which comprises at least on the side comprising a three-dimensional microstructure exposed fibers or threads serving as anchoring for cells.

20. The implant according to claim 1, wherein the substantially closed surface has a porosity at least 10 times lower than the porosity of the fabric.

\* \* \* \* \*

UNITED STATES PATENT AND TRADEMARK OFFICE
CERTIFICATE OF CORRECTION

PATENT NO. : 6,447,551 B1
DATED : September 10, 2002
INVENTOR(S) : Helmut Goldmann It is certified that error appears in the above-identified patent and that said Letters Patent is hereby corrected as shown below:

Column 3,
Line 61, "connect ed" should read -- connected --

Column 4,
Line 17, "sur face" should read -- surface --
Line 23, "permeabilty" should read -- permeability --
Line 61, "long term-stable" should read -- long-term stable --

Column 5,
Line 15, "substances," should read -- substance, --
Line 63, "δ" should read -- γ --

Column 6,
Lines 21-22, "penetratable" should read -- penetrable --
Line 56, "yam" should read -- yarn --

Column 8,
Line 30, "kPascal" should read -- kpascal --

Signed and Sealed this

Eleventh Day of February, 2003

JAMES E. ROGAN
*Director of the United States Patent and Trademark Office*